(12) United States Patent
Dershem

(10) Patent No.: US 7,678,879 B2
(45) Date of Patent: Mar. 16, 2010

(54) ADHESIVE COMPOSITION OF PHENOL-FUNCTIONAL POLYAMIDES

(75) Inventor: Stephen M. Dershem, San Diego, CA (US)

(73) Assignee: Designer Molecules, Inc., San Diego, CA (US)

( * ) Notice: Subject to any disclaimer, the term of this patent is extended or adjusted under 35 U.S.C. 154(b) by 499 days.

(21) Appl. No.: 11/592,007

(22) Filed: Nov. 1, 2006

(65) Prior Publication Data

US 2008/0103240 A1    May 1, 2008

(51) Int. Cl.
*C07C 231/02* (2006.01)
*C08G 69/26* (2006.01)
*C08L 77/06* (2006.01)
*B32B 33/00* (2006.01)
*C08L 63/02* (2006.01)
*C08L 63/04* (2006.01)

(52) U.S. Cl. .................. 528/347; 428/40.1; 525/420; 525/421; 525/423; 525/426; 525/432; 564/139

(58) Field of Classification Search ............ None
See application file for complete search history.

(56) References Cited

U.S. PATENT DOCUMENTS

2006/0122306 A1 *  6/2006  Stafford et al. ............. 524/440
2008/0050602 A1 *  2/2008  Spraul et al. ............ 428/479.6

OTHER PUBLICATIONS

HCAPLUS accession No. 2009:587748 for U.S. Publication No. 2005/0181455, Alberte et al., Aug. 18, 2005, 11 pages.*

* cited by examiner

*Primary Examiner*—Robert Sellers
(74) *Attorney, Agent, or Firm*—The Law Office of Jane K. Babin, Professional Corporation; Jane K. Babin

(57) ABSTRACT

The invention is based on the discovery that the compounds and compositions described herein are useful as film-forming adhesives for use in a variety of applications, including, for example, adhesive tapes for the electronic packaging industry. The invention compositions described herein can be cured in a variety of ways with or without a catalyst.

4 Claims, No Drawings

ADHESIVE COMPOSITION OF PHENOL-FUNCTIONAL POLYAMIDES

FIELD OF THE INVENTION

The present invention relates to thermosetting adhesive compositions, methods of preparation and uses therefor. In particular, the present invention relates to thermosetting compositions useful as film forming adhesives.

BACKGROUND OF THE INVENTION

Adhesive compositions are used for a variety of purposes in the fabrication and assembly of semiconductor packages and microelectronic devices. The more prominent uses include bonding of electronic elements such as integrated circuit chips to lead frames or other substrates, and bonding of circuit packages or assemblies to printed wire boards.

Adhesives used in the electronic packaging industry typically contain a thermosetting resin combined with a filler and some type of curing initiator. These resins are primarily used in the electronics industry for the preparation of non-hermetic electronic packages. Adhesives useful for electronic packaging applications typically exhibit properties such as good mechanical strength, curing properties that do not affect the component or the carrier, and rheological properties compatible with application to microelectronic and semiconductor components. Examples of such packages are ball grid array (BGA) assemblies, super ball grid arrays, IC memory cards, chip carriers, hybrid circuits, chip-on-board, multi-chip modules, pin grid arrays, and the like.

Due to the ever-increasing pressure to reduce the size of semiconductor packages, there has been a recent interest in thin die, and the use of these thin die in stacked packages. In some cases, it has proved challenging to use conventional die-attach pastes with thin semiconductor die. Accordingly, there has been recent interest in the use of film-forming adhesives in the semiconductor packaging industry, especially with respect to thin die.

SUMMARY OF THE INVENTION

The invention is based on the discovery that the compounds and compositions described herein are useful as film-forming adhesives for use in a variety of applications, including, for example, adhesive tapes for the electronic packaging industry. The invention compositions described herein can be cured in a variety of ways with or without a catalyst.

The compounds of the invention are film-forming materials that also serve as epoxy curatives. Typically, the compounds of the invention are low molecular weight, phenol-functional polyamides. The polyamide backbone provides pliable, non-tacky film properties for the un-cured material. Heating these compounds results in their conversion to relatively low viscosity fluids, which are capable of fully wetting the back of silicon devices and the substrates to which they are being bonded. The phenolic residues within the backbone of these oligomers provide reactive sites for the cure of epoxy compounds. Furthermore, these compounds impart toughness to the final thermoset adhesive after cure.

In one embodiment of the invention, there are provided compounds having the structure:

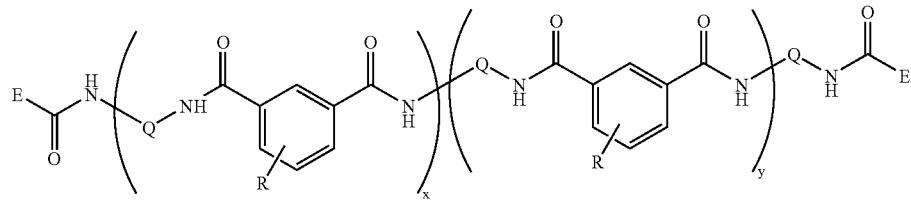

wherein:
each Q is independently aliphatic, cycloaliphatic, aryl, or heteroaryl;
each R is independently H, alkyl, or hydroxyl;
each E is independently a hydroxyl-substituted aryl; and
X and Y are 0 to about 25.

In one embodiment of the invention, there are provided film-forming adhesive compositions including at least one compound of the invention and an epoxy.

In another embodiment of the invention, there are provided die-attach tapes including at least one compound of the invention.

In other embodiments, there are provided assemblies including a first article permanently adhered to a second article by the die-attach tapes of the invention. wherein the first article and the second article are separated only by the adhesive composition applied in (a), and thereafter,
(c) subjecting the assembly to conditions suitable to cure the adhesive composition.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting.

The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, and formulation.

Polyamides have been well known for their outstanding properties in commercial applications for several years. The best know members of this class of polymers are know as "Nylon". Nylons are a class of crystalline solids that are know for their durability, high strength, flexibility, and especially high tensile strength. The crystallinity of these polymers arises from the repeating amide structural unit within their backbone. Hydrogen bonding between these amide repeat units is the basis of this behavior. The presence of this internal hydrogen bonding is also responsible for the superior mechanical properties of the Nylon polyamides. Nylons are also noted for their pronounced water uptake in humid environments. The level of moisture uptake is a direct function of the distance between the amide repeat units.

The polyamide backbone of the compounds of this invention appears to provide an ideal combination of toughness, flow during cure, non-tackiness at room temperature and hydrolytic resistance. The increased hydrocarbon segment length between amide residues for the compounds of this invention results in a dramatic reduction in moisture uptake. Amide bonds are known for being fairly resistant to hydrolysis. The hydrolytic resistance of the amide linkages is further enhanced by the inherent hydrophobicity of the compounds of this invention. The polyamides of this invention are distinguished from the classic Nylons in that they have both relatively long hydrocarbon segment lengths and low molecular weight. The materials of this invention benefit from the low tack imparted by the amide hydrogen bonding-based crystallinity and from the inherent hydrophobicity of the long hydrocarbon segment length. Furthermore, the relatively low molecular weight of these oligomers permits the oligomers to flow and wet well, at or below the cure temperatures used for developing the adhesive bond.

The structure of these compounds can be tailored to provide a range of crosslink densities. The phenolic residues can be placed exclusively at the end of the polyamide oligomers to provide maximum toughening properties. Alternatively, the phenolic residues can be distributed along the backbone to provide higher crosslink density. End-functional, low crosslink density, oligomers are generally desirable where low stress and low modulus adhesives are required. Oligomers with phenolic residues distributed along the backbone are most desirable where high modulus, maximum retention of properties at high temperature, and high adhesion are required.

The optimum functional density of the phenolic residues will also be dependant upon the nature of the epoxy. Low functionality epoxies (e.g. where the number of epoxy groups is around two per molecule) will generally require the use of a higher functional density of phenolic residues in the polyamide curative. Epoxy compounds comtemplated for use for use in combination with the curatives of this invention typically will have at least three epoxy residues per molecule.

In one embodiment, there are provided compounds having the structure

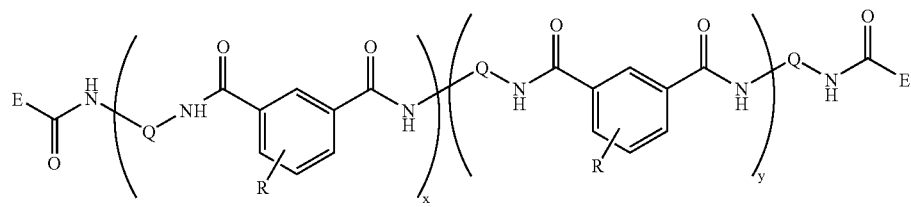

wherein:
    each Q is independently aliphatic, cycloaliphatic, aryl, or heteroaryl;
    each R is independently H, alkyl, or hydroxyl;
    each E is independently a hydroxyl-substituted aryl; and
    X and Y are 0 to about 25.

As used herein, "alkyl" and/or "aliphatic" refers to straight or branched chain hydrocarbyl groups having from 1 up to about 100 carbon atoms. Whenever it appears herein, a numerical range, such as "1 to 100" or "$C_1$-$C_{100}$", refers to each integer in the given range; e.g., "$C_1$-$C_{100}$ alkyl" means that an alkyl group may comprise only 1 carbon atom, 2 carbon atoms, 3 carbon atoms, etc., up to and including 100 carbon atoms, although the term "alkyl" also includes instances where no numerical range of carbon atoms is designated. "Substituted alkyl" refers to alkyl groups further bearing one or more substituents as set forth below. In addition, as used herein "$C_{36}$" refers to all possible structural isomers of a 36 carbon aliphatic moiety, including branched isomers and cyclic isomers.

As used herein, "cycloalkyl" refers to cyclic ring-containing groups containing in the range of about 3 up to 15 carbon atoms, and "substituted cycloalkyl" refers to cycloalkyl groups further bearing one or more substituents as set forth below.

As used herein, "alkenyl" refers to straight or branched chain hydrocarbyl groups having at least one carbon-carbon double bond, and having in the range of about 2 up to 12 carbon atoms, and "substituted alkenyl" refers to alkenyl groups further bearing one or more substituents as set forth below.

As used herein, "alkynyl" refers to straight or branched chain hydrocarbyl groups having at least one carbon-carbon triple bond, and having in the range of about 2 up to 12 carbon atoms, and "substituted alkynyl" refers to alkynyl groups further bearing one or more substituents as set forth below.

As used herein, "aryl" refers to aromatic groups having in the range of 6 up to 14 carbon atoms and "substituted aryl" refers to aryl groups further bearing one or more substituents as set forth below.

As used herein, "alkylaryl" refers to alkyl-substituted aryl groups and "substituted alkylaryl" refers to alkylaryl groups further bearing one or more substituents as set forth below.

As used herein, "arylalkyl" refers to aryl-substituted alkyl groups and "substituted arylalkyl" refers to arylalkyl groups further bearing one or more substituents as set forth below.

As used herein, "arylalkenyl" refers to aryl-substituted alkenyl groups and "substituted arylalkenyl" refers to arylalkenyl groups further bearing one or more substituents as set forth below.

As used herein, "arylalkynyl" refers to aryl-substituted alkynyl groups and "substituted arylalkynyl" refers to arylalkynyl groups further bearing one or more substituents as set forth below.

As used herein, "aroyl" refers to aryl-carbonyl species such as benzoyl and "substituted aroyl" refers to aroyl groups further bearing one or more substituents as set forth below.

As used herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth below.

As used herein, "acyl" refers to alkyl-carbonyl species.

As used herein, "halogen" refers to fluoride, chloride, bromide or iodide atoms.

Substituted aliphatic, aryl, or heteroaryl moieties include, but are not limited to substituents selected from alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, amido, —C(O)H, —C(O)—, —C(O)—, —S—, —S(O)$_2$, —OC(O)—O—, —NR—C(O), —NR—C(O)—NR, —OC(O)—NR, wherein R is H or lower alkyl, acyl, oxyacyl, carboxyl, carbamate, sulfonyl, sulfonamide, sulfuryl, and the like.

The $C_{36}$ diamine may be replaced in whole, or in part by other aliphatic or aromatic diamines in the preparation of these epoxy curative oligomers. Examples of other diamines include amine-terminated (hydrogenated or non-hydrogenated) polybutadienes; amine-terminated butadiene-acrylonitrile resins (Hycar resins); 1,12-diaminododecane; isophoronediamine; 1,6-hexanediamine; methylenedianiline; 4,4-oxydianiline; 3,4'-oxydianiline; tricyclodecanedimethyleneamine, and the like.

Exemplary compounds according to the invention include

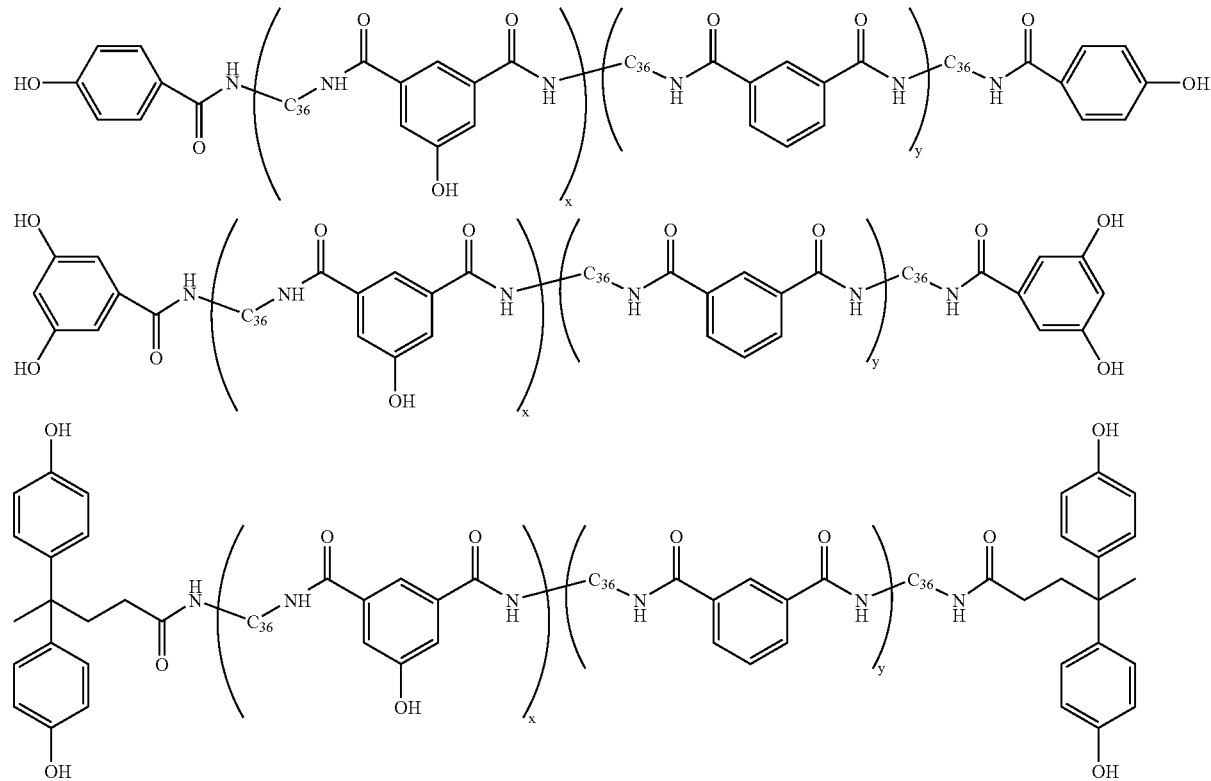

wherein:
X and Y are 0 to about 25;
and

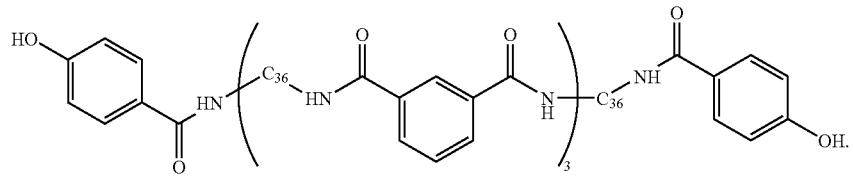

In a further embodiment, there are provided film-forming adhesive compositions including an invention compound and at least one epoxy. Epoxies contemplated for use in the practice of the invention include phenolics, novalacs (both phenolic and cresolic) and the like.

Additional exemplary epoxy resins contemplated for use in the practice of the invention include include N,N-diglycidyl aniline, N,N-diglycidyl-4-glycidyloxyaniline, diglycidyl 1,2-cyclohexanedicarboxylate, diglycidyl 1,2,3,4-tetrahydrophthalate, bis(4-glycidyloxyphenyl)methane, 4,4'-isopropylidenediphenol diglycidyl ether, resorcinol diglycidyl ether, substituted biphenyl diglycidyl ethers, substituted naphthalene diglycidyl ethers, and the like, as well as suitable combinations of any two or more thereof.

Further examples of epoxy resins include glycidyl ethers of compounds selected from phenols, cresol formaldehyde, polyhydroxy phenols, polyaromatic phenols, aliphatic alcohols, polyglycols, aromatic amines, and the like, as well as suitable combinations of any two or more thereof.

Exemplary glycidyl ethers of phenols suitable for use as epoxy resins include phenyl glycidyl ethers, cresyl glycidyl ethers, nonylphenyl glycidyl ethers, and p-tert-butylphenyl glycidyl ethers, and the like, as well as suitable combinations of any two or more thereof. Exemplary glycidyl ethers of phenols also include diglycidyl ethers of: bisphenols (e.g., bisphenol A, bisphenol F, bisphenol E, bisphenol M, bisphenol P, and the like), ethylidinebisphenol, dihydroxydiphenyl ether, N,N'-disalicylal-ethylenediamine, arin, bis(4-hydroxyphenyl)sulfone, bis(hydroxyphenyl)sulfide, 1,1-bis(hydroxyphenyl)cyclohexane, 9,19-bis(4-hydroxyphenyl)fluorene, 1,1,1-tris(hydroxyphenyl)ethane, trihydroxytritylmethane, 4,4'-(1-alpha-methylbenzylidene)bisphenol, 4,4'-(1,3-diethylethylene)diphenol, diethylstilbesterol, 4,4'-dihyroxybenzophenone, resorcinol, catechol, tetrahydroxydiphenyl sulfide, and the like, as well as suitable combinations of any two or more thereof.

Exemplary glycidyl ethers of fused ring polyaromatic phenols suitable for use as epoxy compound starting materials include glycidyl ethers of: dihydroxy naphthalene, 2,2'-dihydroxy-6,6'-dinaphthyl disulfide, 1,8,9-trihydroxyanthracene, and the like, as well as suitable combinations of any two or more thereof.

Exemplary glycidyl ethers of aliphatic alcohols suitable for use as epoxy compound starting materials include diglycidyl ethers of 1,4 butanediol, diglycidyl ethers of neopentyl glycol, diglycidyl ethers of cyclohexane dimethanol, trimethyol ethane triglycidyl ethers, trimethyol propane triglycidyl ethers, and the like, as well as suitable combinations of any two or more thereof.

In other embodiments, the film-forming adhesive may contain epoxy diluents. Epoxy diluents contemplated for use in the practice of the present invention include liquid diluents which comprise at least one epoxy group and which have a viscosity which is sufficiently low to permit the liquid diluent to function as a viscosity reducer. Epoxy diluents can have a variety of epoxy equivalent weights (EEW), including EEWs in the range from about 45 to about 250, in a preferred range from about 90 to about 250, or in a presently preferred range from about 100 to about 200. Exemplary epoxy diluents contemplated for use in the practice of the present invention include liquid diluents having in the range of about 1 to about 3 glycidyl groups, with a preferred range of about 1 to about 2 glycidyl groups.

Further examples of epoxy diluents include 1,4-butanediol diglycidyl ether; neopentyl glycol diglycidyl ether; 1,2-epoxy-3-phenoxypropane; benzyl glycidyl ether; glycidyl isopropyl ether; glycidyl isobutyl ether; glycidyl methyl ether; glycidyl 2-methylphenyl ether; glycidyl 4-methoxyphenyl ether; glycidyl 4-nonylphenyl ether; 1,4-cyclohexanedimethanol diglycidyl ether; 4-tert-butylphenyl glycidyl ether; butyl glycidyl ether; tert-butyl glycidyl ether; trimethylolpropane triglycidyl ether; allyl glycidyl ether; and the like; as well as suitable combinations of any two or more thereof.

Epoxy compounds contemplated for use in the practice of the invention also include cycloaliphatic epoxies, such as, for example, cycloaliphatic epoxies derived from oligomers of cyclopentadiene.

The film-forming adhesive compositions described herein may further contain additional compounds. Such compounds include, for example, imides, monomaleimides, bismaleimides, polymaleimides, cyanate esters, vinyl ethers, vinyl esters, vinyl acetates, esters, ureas, amides, olefins (such as ethylenes, propylenes, and the like) siloxanes, cyanoacrylates, styrenes, oxazolines, benzoxazines, oxetanes, and the like, or combinations thereof.

Additional curing agents may be used in the practice of the invention. These optional curing agents include, phenols, polyphenols, anhydrides, and the like. A catalyst may optionally be used in the practice of the invention as well. Certain catalysts contemplated, include for example, compounds which can be employed to catalyze the reaction between a phenolic hydroxyl group and a vicinal epoxide group include, for example, tertiary amines such as, triethylamine, tripropylamine, tributylamine; 2-methylimidazole (such as, for example, the Curezol™ imidazoles available from Air Products), N-methylmorpholine, combinations thereof and the like; quaternary ammonium compounds such as, benzyl trimethyl ammonium chloride, tetrabutylammonium chloride, combinations thereof and the like; phosphines such as triphenylphosphine, tributylphosphine, trilaurylphosphine, trichlorobutylphosphine, trinaphthylphosphine, and the like; and phosphonium compounds such as, ethyltriphenylphosphonium chloride, ethyltriphenylphosphonium bromide, ethyltriphenylphosphonium iodide, ethyltriphenylphosphonium phosphate, ethyltriphenylphosphonium acetate.acetic acid complex, tetrabutylphosphonium chloride, tetrabutylphosphonium bromide, tetrabutylphosphonium iodide, tetrabutylphosphonium phosphate, tetrabutylphosphonium acetate.acetic acid complex, butyltriphenylphosphonium tetrabromobisphenate, butyltriphenylphosphonium bisphenate, butyltriphenylphosphonium bicarbonate, combinations thereof and the like.

In some embodiments, fillers are contemplated for use in the practice of the present invention. These can be electrically conductive and/or thermally conductive. In addition, the fillers may act to modify the rheology of the resulting composition. Examples of suitable electrically conductive fillers which can be employed in the practice of the present invention include silver, nickel, copper, aluminum, palladium, gold, graphite, metal-coated graphite (e.g., nickel-coated graphite, copper-coated graphite, and the like), and the like. Examples of suitable thermally conductive fillers which can be employed in the practice of the present invention include graphite, aluminum nitride, silicon carbide, boron nitride, diamond dust, alumina, and the like. Compounds that act primarily to modify rheology include polysiloxanes (such as polydimethyl siloxanes) silica, fumed silica, alumina, titania, and the like.

As used herein, the term "coupling agent" refers to chemical species that are capable of bonding to a mineral surface and which also contain polymerizably reactive functional group(s) so as to enable interaction with the film-forming adhesive composition. Coupling agents thus facilitate linkage of the film-forming adhesive composition to the substrate to which it is applied.

In some embodiments, both photoinitiation and thermal initiation may be desirable. For example, curing of a photoinitiator-containing adhesive can be started by UV irradiation, and in a later processing step, curing can be completed by the application of heat to accomplish a free-radical cure. Both UV and thermal initiators may therefore be added to the adhesive composition.

In certain embodiments, the film-forming adhesive compositions and/or die-attach tapes may contain compounds that lend additional flexibility and toughness to the resultant cured adhesive film. Such compounds may be any thermoset or thermoplastic material having a Tg of 50° C. or less, and typically will be a polymeric material characterized by free rotation about the chemical bonds, the presence of ether groups, and the absence of ring structures. Suitable such modifiers include polyacrylates, poly(butadiene), polyTHF (polymerized tetrahydrofuran, also known as poly(1,4-butanediol)), CTBN (carboxy-terminated butadiene-acrylonitrile) rubber, and polypropylene glycol.

In yet another embodiment of the invention, there are provided assemblies of components adhered together employing the above-described film-forming adhesive compositions and/or die attach tapes. Thus, for example, assemblies comprising a first article permanently adhered to a second article by the film-forming adhesive composition described herein are provided. Articles contemplated for assembly employing invention compositions include memory devices, ASIC devices, microprocessors, flash memory devices, and the like. Also contemplated are assemblies comprising a microelectronic device permanently adhered to a substrate by the above-described film-forming adhesive composition. Microelectronic devices contemplated for use with invention die attach pastes include copper lead frames, Alloy 42 lead frames, silicon dice, gallium arsenide dice, germanium dice, and the like.

While this invention has been described with respect to these specific examples, it should be clear that other modifications and variations would be possible without departing from the spirit of this invention.

What is claimed is:

1. A compound having the structure

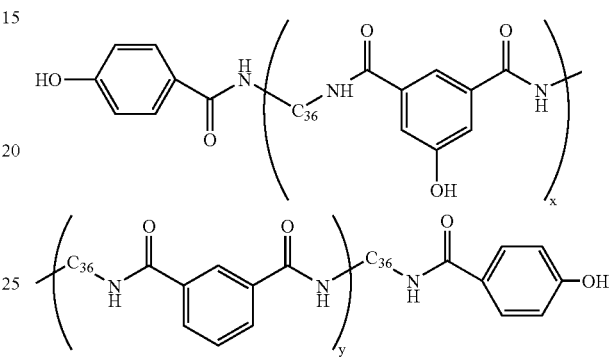

wherein:
X and Y are 0 to about 25.

2. A compound having the structure:

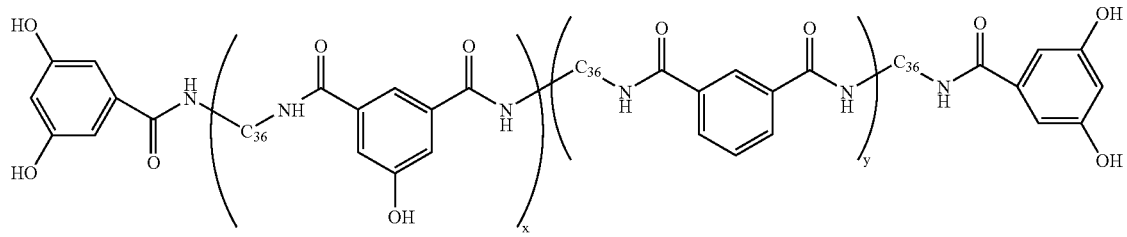

wherein:
X and Y are 0 to about 25.

3. A compound having the structure:

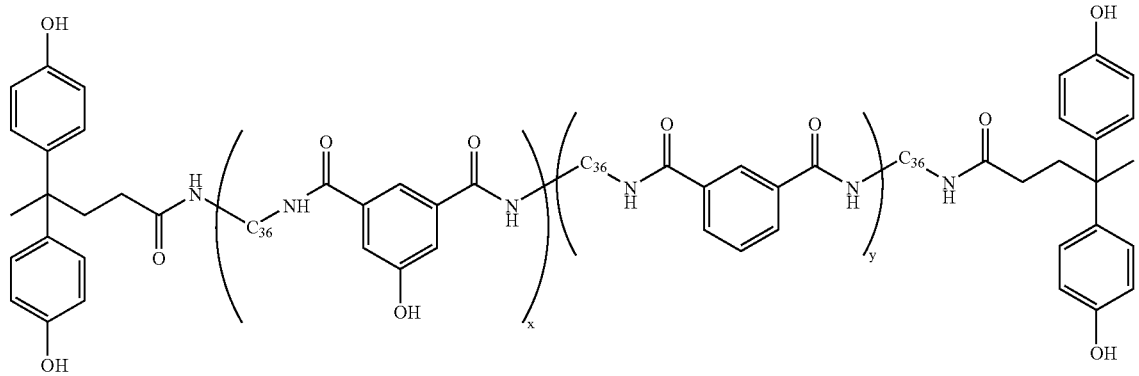

wherein:
   X and Y are 0 to about 25.
   4. A compound having the structure:
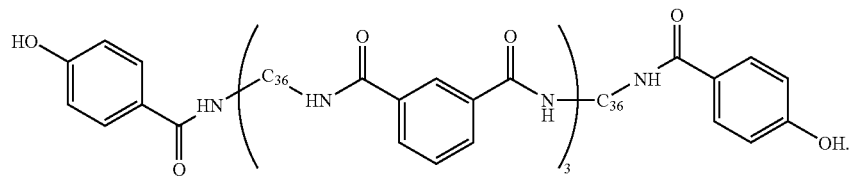
* * * * *